US007566740B2

(12) United States Patent
Libin

(10) Patent No.: US 7,566,740 B2
(45) Date of Patent: *Jul. 28, 2009

(54) METHOD OF TREATING MUCOSITIS

(75) Inventor: Barry Libin, Bellport, NY (US)

(73) Assignee: BML Pharmaceuticals, Inc., Chadds Ford, PA (US)

( * ) Notice: Subject to any disclaimer, the term of this patent is extended or adjusted under 35 U.S.C. 154(b) by 233 days.

This patent is subject to a terminal disclaimer.

(21) Appl. No.: 10/317,633

(22) Filed: Dec. 12, 2002

(65) Prior Publication Data

US 2003/0091515 A1 May 15, 2003

Related U.S. Application Data

(63) Continuation of application No. 09/167,225, filed on Oct. 6, 1998, now abandoned.

(51) Int. Cl.
*A61K 31/085* (2006.01)
*A61K 31/075* (2006.01)
*A61K 31/055* (2006.01)

(52) U.S. Cl. .......................... 514/721; 514/741; 424/49

(58) Field of Classification Search .................. 424/52, 424/54, 49; 514/358, 635, 643, 646, 649, 514/651, 721, 901, 928, 741
See application file for complete search history.

(56) References Cited

U.S. PATENT DOCUMENTS

| | | | | | |
|---|---|---|---|---|---|
| 5,185,377 | A | * | 2/1993 | Schewe et al. | 514/721 |
| 5,213,803 | A | * | 5/1993 | Pollock et al. | 424/440 |
| 5,236,699 | A | * | 8/1993 | Libin | 424/54 |
| 5,407,663 | A | * | 4/1995 | Eisen | 424/49 |
| 5,438,075 | A | * | 8/1995 | Skubitz et al. | 514/563 |
| 5,466,680 | A | * | 11/1995 | Rudy | 514/57 |
| 5,496,828 | A | * | 3/1996 | Cullinan | 514/324 |
| 5,500,448 | A | * | 3/1996 | Cummins et al. | 514/717 |
| 5,716,610 | A | * | 2/1998 | Jack et al. | 424/78.05 |
| 5,772,640 | A | * | 6/1998 | Modak et al. | 604/265 |
| 5,855,872 | A | * | 1/1999 | Libin | 424/49 |
| 5,888,520 | A | * | 3/1999 | Toma et al. | 424/401 |
| 5,945,089 | A | * | 8/1999 | Libin | 424/54 |
| 6,440,395 | B1 | * | 8/2002 | Libin | 424/49 |

FOREIGN PATENT DOCUMENTS

| | | | |
|---|---|---|---|
| CA | 2 132 688 A1 | * | 3/1996 |
| DE | 221080 A1 | * | 4/1980 |
| EP | 679390 A2 | * | 11/1995 |
| EP | 843 002 A2 | * | 5/1998 |
| WO | 86/05391 A1 | * | 9/1986 |
| WO | 93/07250 A1 | * | 4/1993 |
| WO | 97/00667 A1 | * | 1/1997 |
| WO | 97/00668 A1 | * | 1/1997 |

OTHER PUBLICATIONS

Sonis, S.T., "Mucositis as a biological process: a new hypothesis for the development of chemotherapy-induced stomatotoxicity", Oral. Oncol. 34(1):39-43 (Jan. 1998), abstract only as cited through Entrez PubMed Database (last updated May 26, 2005).*
Chemical Abstract 138:297542, "Efficacy of Gelclair in reducing pain in palliative care patients with oral lesions: Preliminary findings from an open pilot study" (2002).*
Chemical Abstract 125:265067, "Benzydamine hydrochloride (Andolex) improves oral mucosal health in the immunocompromised patient" (1996).*
Chemical Abstract 124:278812, "Thalidomide for aphthous ulcers in patients infected with the human immunodeficiency virus" (1996).*
Innocenti, M. et al., "Efficacy of Gelclair in Reducing Pain in Palliative Care Patients with Oral Lesions: Preliminary Finding from an Open Pilot Study". Journal of Pain and Symptom Management, vol. 24, No. 5, (Nov. 5, 2002), pp. 456-457.*
Weidle, P. "Thalidomide for Aphthous Ulcers in Patients Infected with the Human Immunodeficiency Virus" American Journal of Health-System Pharmacy, vol. 53 (Feb. 15, 1996), pp. 368, 371, 372 and 378.*
Arendorf, T. et al., "Benzydamine Hydrochloride (Andolex) Improves Oral Mucosal Health in the Immunocompromised Patient" South African Medical Journal, vol. 86, No. 9 (Sep. 1996), pp. 1136-1137.*
Ferretti et al., Oral Surgery, Oral Medicine and Oral Pathology, "Therapeutic Use of Chlorhexidine in Bone Marrow Transplant Patients: Case Studies", vol. 63, No. 6, Jun. 1987, p. 683-687.*
Ferretti et al., Journal of the American Dental Association, "Chlorhexidine for prophylaxis against oral infections and associated complications in patients receiving bone marrow transplants", vol. 114, Apr. 1987, p. 461-467.*
McGaw et al., Oral Surg Oral Med Oral Pathol, "Oral complications of acute leukemia: prophylactic impact of a chlorhexidine mouth rinse regimen", Sep. 1985;60(3):275-80.*
Kostiala, Current therapeutic research, clinical and experimental, vol. 31, No. 5, pp. 752-753, 1982.*
Budtz-Jorgensen, Journal of Clinical Periodontology, "Hibitane in the treatment of oral candidiasis", vol. 4, No. 5, Dec. 1977, p. 117-128.*
Dreizen et al., Postgraduate Medicine, "Oral Complications of Cancer Radiotherapy", vol. 61, No. 2, Feb. 1977, p. 85-92.*

(Continued)

*Primary Examiner*—Frederick Krass
*Assistant Examiner*—Lezah W Roberts
(74) *Attorney, Agent, or Firm*—James V. Costigan; Hedman & Costigan, P.C.

(57) ABSTRACT

A method of treating mucositis in immunocompromised patients is disclosed which is based on contacting the affected area with an amount of composition which comprises triclosan and a cationic antibacterial agent in amounts which are effective to alleviate the symptoms of mucositis.

7 Claims, No Drawings

OTHER PUBLICATIONS

Levy-Polack et al., Special Care in Dentistry, 18(5) pp. 189-193, 1998.*

Poland, J. M., The American Journal of Hospice Care, 4(4), pp. 27-30, Jul./Aug. 1987.*

Ferretti et al., Bone Marrow Transplantation, 3(5), pp. 483-493, 1988.*

Ferretti et al., Oral Surgery Oral Medicine Oral Pathology, 69(3), pp. 331-338, Mar. 1990.*

Greenspan et al., Oral Surgery Oral Medicine Oral Pathology, 78(2) pp. 211-215, Aug. 1994.*

Yasuda et al., Dermatology, 195(suppl. 2), pp. 19-28, 1997.*

Ciancio, S., Journal of the American Dental Society, 125(suppl. 2), pp. 29S-32S, Aug. 1994. Abstract only.*

Rutkauskas et al., Oral Surgery Oral Medicine Oral Pathology, 76(4), pp. 441-448, Oct. 1993. Abstract only.*

* cited by examiner

METHOD OF TREATING MUCOSITIS

This application is a continuation of application Ser. No. 09/167,225, filed Oct. 6, 1998 now abandoned.

BACKGROUND OF THE INVENTION

Immunodeficient patients frequently exhibit a condition on the oral mucosa which is clinically described as oral mucositis. This condition has no known microbial or viral vector that has been implicated as the causative agent. The immunodeficiency that preceded the appearance of mucositis may arise spontaneously from genetic factors, may be caused by infections, e.g., the HIV virus or mucositis be induced as a result of chemotherapy or radiation therapy for neoplastic diseases. This condition has been difficult to treat and has not responded to treatment with antimicrobial agents.

The applicant has discovered a treatment for mucositis which is based on contacting the diseased sites on the affected area of the mucosa with a combination of triclosan and a cationic antibacterial agent. The present inventor holds U.S. Pat. No. 5,236,699, which is incorporated by reference. That patent describes the use of a mouth rinse which contains triclosan and a cationic antibacterial agent for use inter alia the treatment of plaque and gum diseases.

SUMMARY OF THE INVENTION

The present invention comprises a method of treating mucositis which comprises applying to the affected area an effective amount of a composition which comprises triclosan and a cationic antimicrobial or cationic antibacterial agent.

It is a primary object of the invention to provide a method for treating oral mucositis in immunocompromised patients.

It is also an object of the invention to provide a method for treating mucositis using a combination of triclosan and a cationic antibacterial agent.

These and other objects of the invention will become apparent from a review of the appended specification.

DETAILED DESCRIPTION OF THE PRESENT INVENTION

Mucositis is treated in accordance with the present invention by contacting the involved oral mucosa of an immunocompromised patient who is afflicted with mucositis with a composition which contains an amount of triclosan and a cationic antibacterial compound which is effective to treat mucositis. Generally these compositions contain in combination, about 0.01 to 5.3 wt % and preferably 0.1 to 0.5 wt % of triclosan and about 0.024 to 0.3 wt % and preferably about 0.025 wt % of a cationic antibacterial agent. Generally, semi-solid formulations will be formulated with higher levels of triclosan and the cationic agent. The amount of the combined formulation which is applied will depend on the extent of the lesion. Generally when a liquid formulation is applied to a typical lesion, from 5 ml to 30 ml is applied to the lesion as a mouth rinse with the patient being instructed to eject the excess amount of the formulation from the mouth without swallowing. If a semi-solid formulation is used, then a thin film, i.e. from 0.5 mm to 5 mm in thickness may be applied to the affected area.

Triclosan is 2,4,4'-trichloro-2'-hydroxydiphenyl ether which is commercially available. The cationic antibacterial agents include chlorhexidine and quaternary ammonium salts such as cetylpyridinium chloride (CPC) which is the monohydrate of the quaternary ammonium salt of pyridine and cetyl chloride. CPC is cationic, highly soluble in water and alcohol. Other cationic antimicrobial agents include benzalkonium chloride, benzethonium chloride, methylbenzethonium chloride and domiphen bromide. Chlorhexidine may be applied as the free base, or as the dihydrochloride or the gluconate salt.

The combination of triclosan and the cationic agent has the effect that the combined agents are readily adsorbed and retained on the oral mucosa while resisting removal by saliva in the oral cavity.

The compositions may be prepared as a liquid or a semi-solid formulation. The semi-solid compositions may vary from highly viscous liquids to gels or paste like formulations.

A liquid formulation may be prepared with purified water, the triclosan, the cationic agent and a solubilizer. The solubilizer may comprise a poloxamer. These materials are of the formula $HO(CH_2CH_2O)_a(CH-(CH_3)(CH_2OH)_b(CH_2CH_2O)_cH$ where b is at least 15 and $(CH_2CH_2O)_a+c$ is varied from 20 to 90% by weight and the weight average mol wt ranges from 10,000 to >16,000. The polyoxamers are available under the Pluronic trademark and Pluronic F127 is a preferred solubilizer. If solubilizer is employed, it will comprise from 0.5 to 8 wt % of the liquid composition. Generally, only liquid compositions in water will require a solubilizer; semi-solid formulations will not require the presence of a solubilizer.

The mucositis treating formulation may include an anticaries agent which is soluble in water such as sodium fluoride, stannous fluoride or sodium monofluorophosphate in an amount which is effective to inhibit tooth decay in an immunocompromised patient. Generally, this amount will be from 0.01 to 4% by weight, based on the weight of the fluoride ion. The amount may be varied depending on the particular source of the fluoride ion which is chosen. Certified color may be added in a minor amount e.g. 0.1% by weight. FD&C Blue No. 1 or FD&C Yellow No. 5 may be used as desired.

A typical liquid formulation will comprise:

|   | % weight |
|---|---|
| triclosan | 0.100 |
| CPC | 0.024 |
| Sorbitol Solution, U.S.P. | 12.000 |
| Glycerin | 10.000 |
| Sodium Saccharin, U.S.P | 0.100 |
| Pluronic FI27, NF | 4.000 |
| 190 Proof Grain Alcohol, U.S.P. | 7.000 |
| Peppermint IFL2745 | 0.152 |
| Caramel Color AP100 | 0.0085 |
| Purified water | 66.615 |

A typical fluoridated liquid formulation will comprise:

|   | % weight |
|---|---|
| triclosan | 0.100 |
| CPC | 0.024 |
| Sodium Fluoride | 0.020 |
| Sorbitol Solution, U.S.P. | 11.980 |
| Glycerin | 10.000 |
| Sodium Saccharin, U.S.P | 0.100 |
| Pluronic FI27, NF | 4.000 |
| 190 Proof Grain Alcohol, U.S.P. | 7.000 |
| Peppermint IFL2745 | 0.152 |
| Caramel Color AP100 | 0.0085 |
| Purified water | 66.615 |

A typical semisolid formulation which is a cream: will include:

| | |
|---|---|
| triclosan | 0.1-5.3 wt % |
| Cetaryl glucoside and cetaryl alcohol (Emulgade PL 68/50, Henkel) | 0.5-6.7 wt % |
| Cetaryl alcohol (Lanette, Henkel) | 0.5-7.7 wt % |
| Coco-Caprylate (Cedol LC, Henkel) | 0.5-6.0 wt % |
| Dicapryl ether (Cetiet, Henkel) | 0.25-5.0 wt % |
| Sweet almond oil | 0.25-5.0 wt % |
| Petrolatum | 0.5-6.0 wt % |
| Dimethicone (Silicone DC 200CS/Dow) | 0.1-5 wt % |
| Phase B | |
| CPC | 0.01-4.4 wt % |
| glycerin | 0.5-4.6 wt % |
| Sodium methylparaben/Sodium paraben or | 0.01-0.03 wt % |
| Sodium benzoate | 0.25-0.3 wt % |
| Deionized water | 10-90 wt % |

An example of a semi-solid formulation according to the invention is as follows:

| | |
|---|---|
| Phase A | |
| triclosan | 0.3 wt % |
| Cetaryl glucoside and cetaryl alcohol (Emulgade PL 68/50, Henkel) | 3.7 wt % |
| Cetaryl alcohol (Lanette, Henkel) | 3.7 wt % |
| Coco-Caprylate (Cedol LC, Henkel) | 3.0 wt % |
| Dicapryl ether (Cetiet, Henkel) | 2.0 wt % |
| Sweet almond oil | 2.0 wt % |
| Petrolatum | 3.0 wt % |
| Dimethicone (Silicone DC 200CS/Dow) | 0.6 wt % |
| Phase B | |
| CPC | 0.1 wt % |
| Glycerin | 2.6 wt % |
| Sodium methylparaben | 0.18 wt % |
| Sodium paraben | 0.02 wt % |
| Deionized water to | 100.0 wt % |
| Phase C | |
| Tocopheryl acetate (cophenol 1260/Henkel) | 1.0 wt % |

The composition is prepared by separately heating Phase A and Phase B to 80° C. prior to forming these phases. Phase C is added with stirring at 55° C. until a smooth homogeneous mixture is obtained.

The foregoing description of a preferred embodiment of the invention has been presented for purposes of illustration and description. It is not intended to be exhaustive or to limit the invention to the precise form disclosed. Obvious modifications or variations are possible in light of the above teachings. All such obvious modifications and variations are intended to be within the scope of the appended claims.

I claim:

1. A method of treating mucositis in an immunocompromised patient, said method comprising contacting a mucositis lesion in said patient with an amount of a composition which comprises triclosan and a cationic antibacterial agent which is effective to alleviate the symptoms of mucositis.

2. A method of treating mucositis as defined in claim 1 wherein the cationic agent is selected from the group consisting of chlorhexidine, cetylpyridium chloride, benzalkonium chloride, benzethonium chloride, methylbenzethonium chloride and domiphen bromide.

3. A method of treating mucositis as defined in claim 1 wherein the cationic agent is cetylpyridium chloride.

4. A method of treating mucositis as defined in claim 3 wherein the triclosan and cationic agent are combined in a liquid formulation with a solubilizer.

5. A method of treating mucositis as defined in claim 3 wherein the triclosan and the cationic agent are combined in a semi-solid formulation.

6. A method of treating mucositis in an immunocompromised patient, said method comprising contacting a mucositis lesion in said patient with an amount of a composition which consists essentially of triclosan and a cationic antibacterial agent in amounts which are effective to alleviate the symptoms of mucositis.

7. A method of treating mucositis in an immunocompromised patient, said method consisting essentially of contacting a mucositis lesion in said patient with an amount of a composition which consists essentially of triclosan and a cationic antibacterial agent which is effective to alleviate the symptoms of mucositis.

* * * * *